(12) United States Patent
Venn-Watson

(10) Patent No.: US 9,561,206 B2
(45) Date of Patent: *Feb. 7, 2017

(54) USE OF HEPTADECANOIC ACID (C17:0) TO DETECT RISK OF AND TREAT HYPERFERRITINEMIA AND METABOLIC SYNDROME

(71) Applicant: Stephanie Venn-Watson, San Diego, CA (US)

(72) Inventor: Stephanie Venn-Watson, San Diego, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/591,660

(22) Filed: Jan. 7, 2015

(65) Prior Publication Data

US 2016/0193170 A1    Jul. 7, 2016

(51) Int. Cl.
| | |
|---|---|
| *A61K 31/20* | (2006.01) |
| *G01N 33/92* | (2006.01) |
| *A61K 31/201* | (2006.01) |
| *A61K 31/202* | (2006.01) |

(52) U.S. Cl.
CPC ............ *A61K 31/20* (2013.01); *A61K 31/201* (2013.01); *A61K 31/202* (2013.01); *G01N 33/92* (2013.01); *G01N 2405/00* (2013.01); *G01N 2800/04* (2013.01); *G01N 2800/042* (2013.01); *G01N 2800/22* (2013.01); *G01N 2800/50* (2013.01)

(58) Field of Classification Search
CPC .................................................... A61K 31/20
See application file for complete search history.

(56) References Cited

FOREIGN PATENT DOCUMENTS

| WO | 2005/099483 A1 | 10/2005 |
| WO | 2006/038063 A1 | 4/2006 |

OTHER PUBLICATIONS

Forouhi, Nita G. et al., "Differences in the Prospective Association Between Individual Plasma Phospholipid Saturated Fatty Acids and Incident Type 2 Diabetes: The EPIC-InterAct Case-Cohort Study", Lancet Diabetes Endocrinal 2014: vol. 2, pp. 810-818 (2014).

Krachler, Benno et al., "Fatty Acid Profile of the Erythrocyte Membrane Preceding Development of Type 2 Diabetes Mellitus", Nutrition, Metabolism & Cardiovascular Diseases, vol. 18, pp. 503-510 (2008).

Maruyama, Chizuko et al., "Differences in Serum Phospholipid Fatty Acid Compositions and Estimated Desaturase Activities Between Japanese Men With and Without Metabolic Syndrome", Journal of Atherosclerosis and Thrombosis, vol. 15, No. 6, pp. 306-313 (2008).

Magnusdottir, OK et al., "Plasma Alkylresorcinols C17:0/C21:0 Ratio, A Biomarker of Relative Whole-Grain Rye Intake, Is Associated to Insulin Sensitivity: A Randomized Study", European Journal of Clinical Nutrition vol. 68, pp. 453-458 (2014).

Venn-Watson, Stephanie et al., "Investigation of Fish-Based Nutrients to Protect Against Metabolic Syndrome in Bottlenose Dolphins (*Tursiops truncatus*)", presentation at International Association for Aquatic Animal Medicine (IAAAM), Gold Coast, Austrailia, May 2014.

Lagerstedt, Susan A. et al., "Quantitative Determination of Plasma C8-C25 Total Fatty Acids for the Biochemical Diagnosis of Nutritional and Metabolic Disorders", Molecular Genetics and Metabolism, vol. 73, pp. 38-45 (2001).

Venn-Watson, Stephanie et al., "Reversion of Hyperferritinemia and Prediabetes With Dietary Margaric Acid", 2014.

International Search Report and Written Opinion issued Mar. 29, 2016 for PCT/US2015/067172.

Valenti, et al., "[769] Iron Depletion by phlebotomy improves insulin resistance in patients with nonalcoholic fatty liver disease and hyperferritinemia; evidence from a case control study", Journal of Hepatology, Elsevier, Amsterdam, NL, vol. 46, Apr. 2007, pp. S288-S289.

Grundy Scott M., et al. "Definition of metabolic syndrome: Report of the National Heart, 5 Lung and Blood Institute/American Heart Association conference on scientific issues related to definition", Circulation, Lippincott Williams & Wilkins, US, vol. 109, No. 3, Jan. 27, 2004 (Jan. 27, 2004), pp. 433-438.

*Primary Examiner* — Sun Jae Yoo
(74) *Attorney, Agent, or Firm* — SSC Pacific Patent Office; Arthur K. Samora; Kyle Eppele

(57) ABSTRACT

Methods for detecting risks for and/or causes of metabolic syndrome or hyperferritinemia in accordance with several embodiments can include the step of measuring the level of heptadecanoic acid in a blood sample of a subject. The methods of several embodiments can further include the step of deeming the subject as having or being at risk of metabolic syndrome if the amount of heptadecanoic acid is below 0.4% of all fatty acids in the sera or plasma. The methods for treating metabolic syndrome or hyperferritinemia according to several embodiments can also include the step of administering a daily dose of heptadecanoic acid to a subject suffering from metabolic syndrome or hyperferritinemia for a period of time from three weeks to twenty-four weeks, wherein the minimum daily dose comprises about 3 mg per lb (or 6 mg per kg) of body weight.

2 Claims, 8 Drawing Sheets

USE OF HEPTADECANOIC ACID (C17:0) TO DETECT RISK OF AND TREAT HYPERFERRITINEMIA AND METABOLIC SYNDROME

FEDERALLY-SPONSORED RESEARCH AND DEVELOPMENT

The United States Government has ownership rights in this invention, pursuant to passing of title to a Subject Invention under Federal Grant N00014-12-1-0294 (National Marine Mammal Foundation). Licensing inquiries may be directed to Office of Research and Technical Applications, Space and Naval Warfare Systems Center, Pacific, Code 72120, San Diego, Calif., 92152; telephone (619) 553-5118; email: ssc pac t2@navy.mil, referencing NC 103395.

FIELD OF THE INVENTION

The present invention pertains generally to the detection and treatment of metabolic syndrome and hyperferritinemia. More particularly, the present invention pertains to the detection and treatment of metabolic syndrome and hyperferritinemia by measuring and raising (if necessary) the level of heptadecanoic acid in the blood of a subject.

BACKGROUND OF THE INVENTION

There is a worldwide pandemic of diabetes in humans. In addition to diabetes, more than one in every three adults in the United States, an estimated 86 million people have metabolic syndrome, also called prediabetes. An estimated 440 million people in the world will possibly have diabetes by 2030, and there is a dire need to stem concurrent pandemics of metabolic syndrome, type 1 diabetes and type 2 diabetes.

In human subjects, high serum ferritin and iron overload have also been associated with metabolic syndrome, type 2 diabetes, and type 1 diabetes. While iron overload is most commonly associated with a mutation in the HFE gene resulting in C282Y substitutions, there is increasing recognition of high serum ferritin that is not associated with known genetic mutations. Ferritin is a measurement of total iron body stores. High ferritin in the blood (i.e. hyperferritinemia) and associated iron overload have been associated with metabolic syndrome (prediabetes), type 2 diabetes and type 1 diabetes in humans. Until now, serum ferritin has not been routinely tested in human subjects, but the few screening studies known in the prior art have demonstrated that a surprisingly high percent (28% and 12%) of healthy elderly men and women in the United States have hyperferritinemia. It is unknown precisely how high ferritin increases the risk of diabetes, but proposed mechanisms include direct injury to the liver and pancreas from excessive deposition or indirect injury from increased oxidative radicals.

Like human subjects, bottlenose dolphin (*Tursiops truncatus*) subjects can also be susceptible to metabolic syndrome, including high insulin, glucose, triglycerides, fatty liver disease, and iron overload. Iron overload in dolphins, involving excessive iron deposition primarily in the liver's Kupffer cells, can be progressive with age and can be associated with elevated insulin, lipids, and liver enzymes. This disease is associated with neither mutations in the HFE gene nor increases in studied acute phase proteins. Similar to humans, iron overload in dolphins is treated with phlebotomy, and repeated treatments are needed throughout life due to returning elevations of serum ferritin. The underlying causes of iron overload and hyperferritinemia in dolphins are unknown.

Dolphins at the Navy Marine Mammal Program (MMP) are a well-studied dolphin population with regard to metabolic syndrome, and this population has a higher risk of developing metabolic syndrome when compared to wild dolphins, such as wild dolphins living in Sarasota Bay, Fla., for example. When comparing the two populations, neither body mass indices nor stress indices (i.e. cortisol) are risk factors for metabolic syndrome in MMP dolphins. In studies comparing values of blood-based indicators of metabolic syndrome, MMP dolphins have been older than Sarasota Bay dolphins; older age of the MMP dolphin population is further supported by its higher annual survival rates and longer lives compared to wild dolphins, including those living in Sarasota Bay. Proposed risk factors for metabolic syndrome in dolphins can include advanced age, differences in feeding and activity schedules, and differences in dietary fish. It can be hypothesized that differences in dietary fish (and certain fatty acids associated with particular types of fish) can be responsible for differences in the risk of metabolic syndrome and iron overload in dolphins.

In view of the above, it is an object of the present invention to provide a method for detecting protective and risk factors against and for metabolic syndrome and hyperferritinemia in mammal subjects such as dolphins and humans. Another object of the present invention is to provide a method for treating metabolic syndrome and/or hyperferritinemia in mammal subjects, such as dolphins and humans. Still another object of the present invention is to provide a method for detecting metabolic syndrome and/or hyperferritinemia in mammal subjects, such as for dolphins and humans that increases the level of heptadecanoic acid of the subject sera. Yet another object of the present invention is to provide a method for detecting and treating hyperferritinemia without resorting to phlebotomy. Another object of the present invention is to provide a method for detecting and treating metabolic syndrome and/or hyperferritinemia in mammal subjects, such as dolphins and humans that is easy to accomplish in a cost-effective manner.

SUMMARY OF THE INVENTION

Methods for detecting risk factors for metabolic syndrome or hyperferritinemia in accordance with several embodiments can include the step of measuring the level of heptadecanoic acid (also called C17:0 or margaric acid) in a blood sample of a subject. The methods of several embodiments can further include the step of deeming the subject as having risk factors for or causes of metabolic syndrome if the amount of heptadecanoic acid represents below 0.4% of the total fatty acids present in the serum or plasma. The methods for treating metabolic syndrome or hyperferritinemia according to several embodiments can also include the step of administering a daily dose of heptadecanoic acid to a subject suffering from metabolic syndrome or hyperferritinemia for a period of time from three weeks to twenty-four weeks, with continuous daily doses thereafter to prevent recurrence, wherein the total daily dose comprises an approximate minimum of 3 mg heptadecanoic acid per lb (or 6 mg heptadecanoic per kg) of mammal body weight. The administration of heptadecanoic acid according to several embodiments can also treat hyperferritinemia without requiring phlebotomy.

BRIEF DESCRIPTION OF THE DRAWINGS

The novel features of the present invention will be best understood from the accompanying drawings, taken in conjunction with the accompanying description, in which similarly-referenced characters refer to similarly-referenced parts, and in which.

DETAILED DESCRIPTION OF THE EMBODIMENTS

Figure 1:
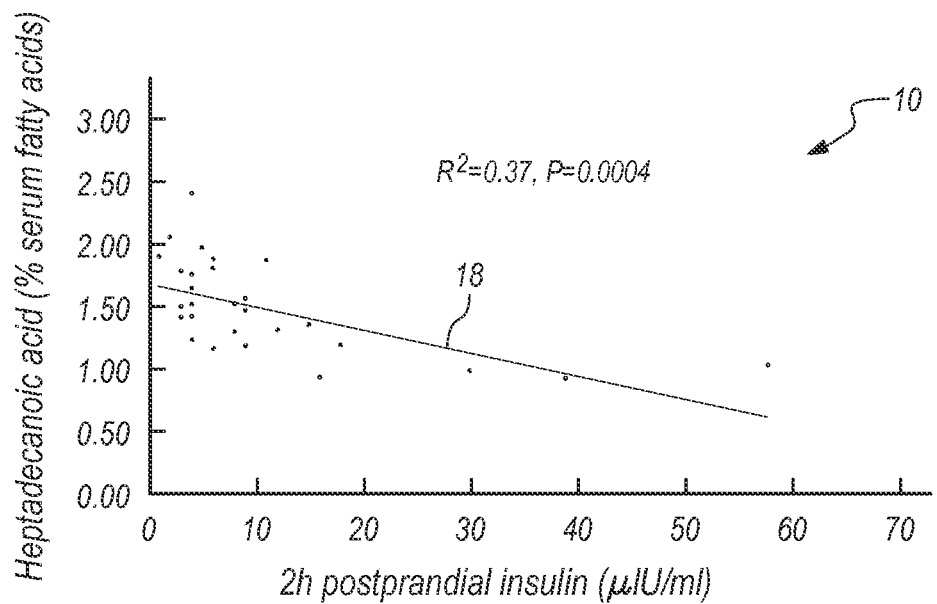
FIGS. 1-4 are graphs that illustrate significant, inverse linear associations between heptadecanoic acid (as % serum fatty acids) and insulin, glucose, triglycerides, and ferritin, respectively, using simple linear regression models.
Figure 2:
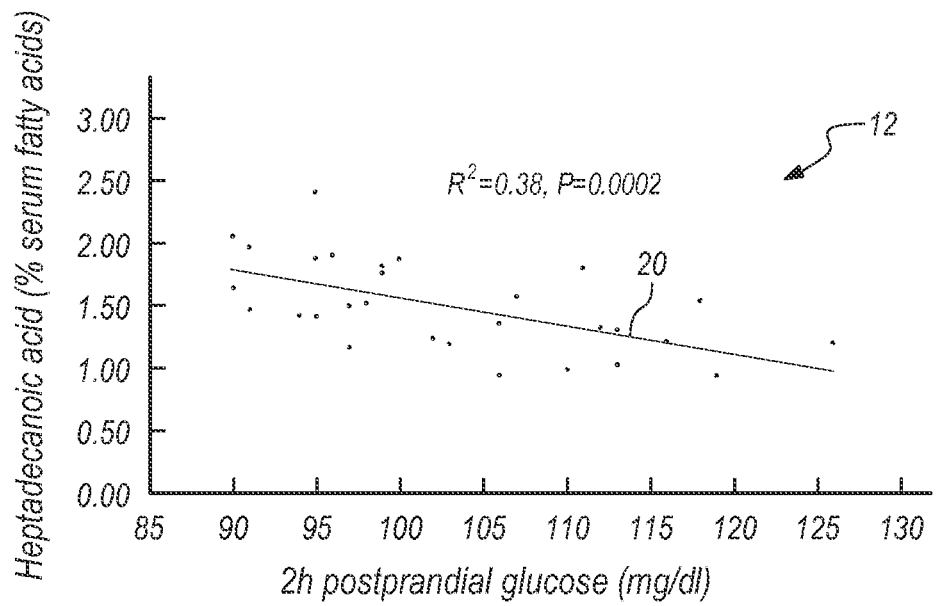
Figure 3:
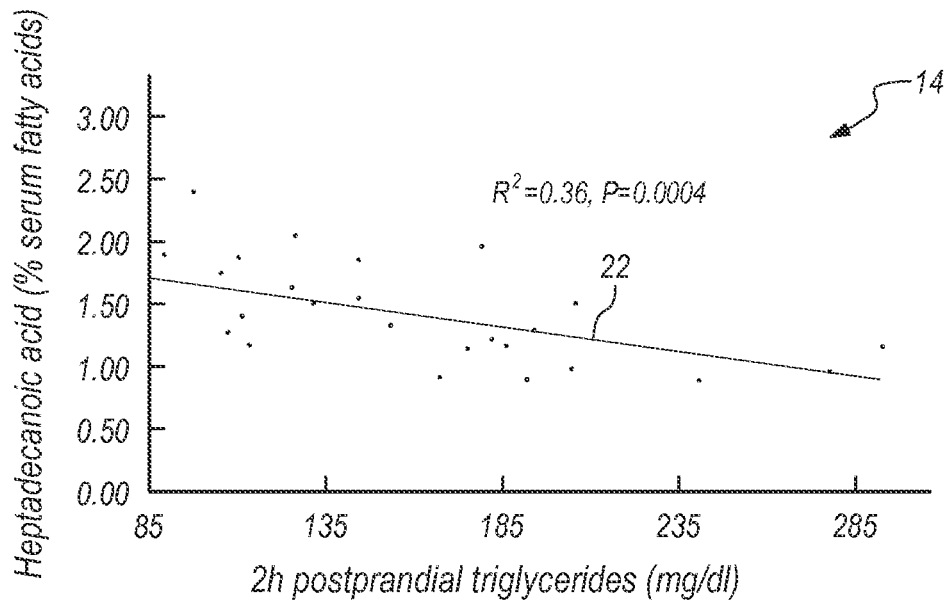
Figure 4:
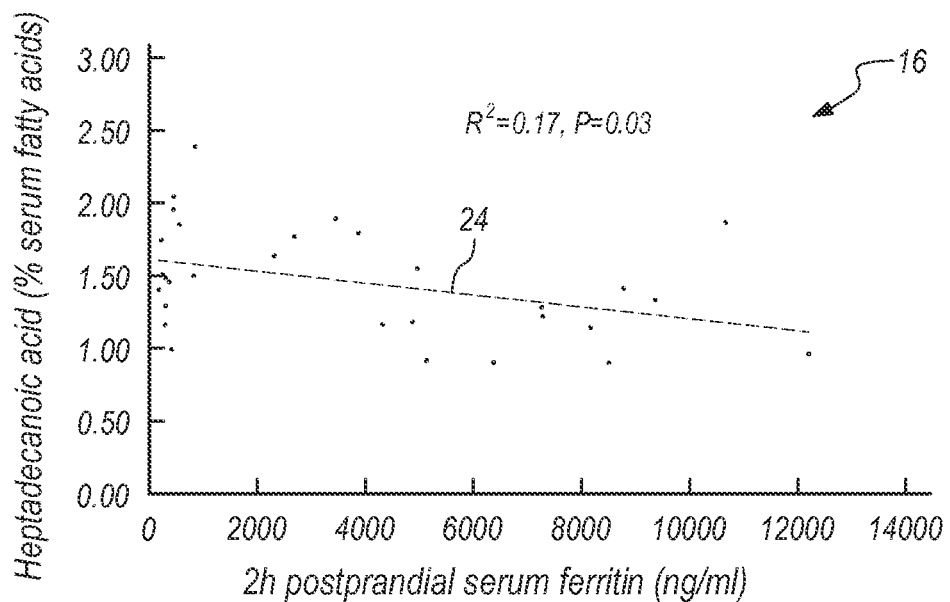

Serum fatty acids and metabolic syndrome indices

Table 1 is a table of blood values of blood samples that were taken from a managed population of thirty dolphins from the Navy Marine Mammal Program (MMP). Dolphins at the Navy Marine Mammal Program (MMP) are a well-studied dolphin population with regard to metabolic syndrome, and this population has a higher risk of developing metabolic syndrome when compared to wild dolphins, such as wild dolphins living in Sarasota Bay, Fla., for example. 2 h postprandial blood values from MMP dolphins with elevated insulin (Elevated insulin levels were defined as values greater than or equal to the 75th quartile among the 30 Group A dolphins (15 µIU/ml), n=8) were compared to MMP dolphins without elevated insulin (n=22). Table 1 illustrates values of elevated versus non-elevated insulin. There were no differences in groups with regard to age (30±7 and 25±14 years, respectively; P=0.32) or sex (percent female 37.5% and 54.6%, respectively; P=0.68). Similar to what has been previously reported with MMP dolphins, those with elevated insulin were also more likely to have higher glucose, triglycerides, and gamma-glutamyl transpeptidase (GGT) when compared to MMP dolphins with non-elevated insulin, which can support the proposition that dolphins with elevated insulin represent those with or at higher risk of metabolic syndrome.

TABLE 1

| Metabolic variable | Elevated insulin (n = 8) | Non-elevated insulin (n = 22) | P value |
|---|---|---|---|
| Metabolic panel | | | |
| Glucose (mg/dl) | 114 ± 7 | 100 ± 8 | 0.002 |
| Triglycerides (mg/dl) | 164 ± 205 | 128 ± 43 | 0.007 |
| Gamma-glutamyl transpeptidase (U/l) | 33 ± 12 | 24 ± 10 | 0.046 |
| Iron (µg/dl) | 178 ± 39 | 177 ± 63 | 0.64 |
| Ferritin (ng/ml) | 5,931 ± 4,210 | 3,131 ± 3,371 | 0.13 |
| Transferrin saturation (%) | 53 ± 14 | 57 ± 21 | 1.0 |
| HbA1c (%) | 5.1 ± 0.2 | 5.2 ± 0.4 | 0.78 |
| Estimated average glucose (mg/dl) | 85 ± 7 | 86 ± 12 | 0.78 |
| Serum fatty acid (%) | | | |
| Heptadecanoic acid (C17:0) | 1.0 ± 0.2 | 1.6 ± 0.3 | 0.0008 |
| Oleic acid (C18:1n9) | 21 ± 2 | 18 ± 4 | 0.03 |
| Linoleic acid (C18:2n6) | 1.6 ± 0.1 | 1.3 ± 0.2 | 0.03 |
| Arachidonic acid (C20:4n6) | 3 ± 0.3 | 4 ± 1 | 0.004 |
| Eicosapentaenoic acid (C20:5n3) | 10 ± 1 | 13 ± 3 | 0.006 |
| Myristic acid (C14:0) | 1.7 ± 0.4 | 1.9 ± 0.6 | 0.39 |
| Palmitic acid (C16:0) | 14 ± 1 | 14 ± 2 | 0.25 |
| Palmitoleic acid (C16:1n7) | 6 ± 1 | 6 ± 1 | 0.17 |
| Stearic acid (C18:0) | 12 ± 2 | 11 ± 2 | 0.66 |
| Vaccenic acid (C18:1cis-11n7) | 6 ± 2 | 6 ± 1 | 0.73 |
| α-Linolenic acid (C18:3n3) | 0.2 ± 0.1 | 0.4 ± 0.7 | 0.28 |
| Erucic acid (C22:1n9) | 4.7 ± 1.7 | 4.6 ± 1.3 | 0.87 |
| Docosatrienoic acid (C22:3n3) | 0.1 ± 0.1 | 0.1 ± 0.1 | 0.47 |
| Docosapentaenoic acid (C22:5n3) | 1.9 ± 0.1 | 2.0 ± 0.3 | 0.98 |
| Docosahexaenoic acid (C22:6n3) | 9.2 ± 0.9 | 8.9 ± 1.2 | 0.34 |
| Tricosylic acid (C23:0) | 0.5 ± 0.1 | 0.5 ± 0.3 | 0.32 |
| Nervoic acid (C24:1n9) | 1.0 ± 0.5 | 0.9 ± 0.4 | 0.76 |

From Table 1 above, it can be seen that dolphins with elevated insulin also had higher oleic acid and linoleic acid; and lower heptadecanoic acid, arachidonic acid, and EPA compared to non-elevated insulin dolphins. Thus, the methods of the present invention can focus on these five fatty acids, and margaric acid in particular (in the specification, heptadecanoic acid, margaric acid and C17:0 shall be taken to mean the same thing). The complete set of data can be found in the paper by Stephanie Venn-Watson et al. entitled "Reversion of Hyperferritinemia and Prediabetes with Dietary Margaric Acid", which is included in Applicant's Invention Disclosure Statement. This paper is incorporated by reference into this application. The manner in which the serum and red blood cell fatty acid profiles was accomplished is described more fully in a paper by Susan A. Lagerstedt et al. entitled "Quantitative Determination of Plasma C8-C26 Total Fatty Acids for the Biochemical Diagnosis of Nutritional and Metabolic Disorders".

Referring now to FIGS. 1-4, FIGS. 1-4 are plots 10, 12, 14, and 16 of margaric acid (as a percentage of serum fatty acids in sera) versus 2 h postprandial insulin (µIU/ml), glucose (mg/dl), triglycerides (mg/dl) and ferritin (ng/ml), respectively, for the 30 MMP dolphins cited above. For each of the respective plots 10, 12, 14 and 16 in FIGS. 1-4, respective linear regressions 18, 20, 22 and 24 of the data were accomplished.

The statistical analyses depicted in FIGS. 1-4 were conducted using the World Programming System (World Programming Ltd., Hampshire, United Kingdom). Age, sex, and blood values (glucose, HbA1c, estimated average blood glucose, triglycerides, GGT, iron, transferrin saturation, ferritin, and percent serum fatty acids) were compared between dolphins with and without elevated insulin. Sex distribution was compared using a Mantel-Haenzsel Chi-square test. Age and blood variable values were compared using a Wilcoxon rank-sum test. For the five fatty acids that had significant differences between dolphins with and without elevated insulin (heptadecanoic acid, oleic acid, linoleic acid, arachidonic acid (AA), and eicosapentaenoic acid (EPA)), simple linear and stepwise multivariate regressions were used to test for associations between these potential fatty acid predictors and dependent metabolic syndrome indices (insulin, glucose, triglycerides, and ferritin). In all analyses, significance was defined as a P value less than 0.05.

From FIGS. 1-4, and using the above criteria, it can be seen that among the 30 MMP dolphins, percent serum heptadecanoic acid had negative linear associations with insulin, glucose, triglycerides, and ferritin, respectively. Using the best fit, stepwise regression described above, it can be inferred from FIGS. 1-4 that heptadecanoic acid can be an independent predictor of insulin (FIG. 1, P=0.0004), glucose (FIG. 2, P=0.0002) triglyceride (FIG. 3, P=0.0004), and ferritin (FIG. 4, P<0.0001) levels.

From the data above, it can be appreciated that there is a linear relationship between levels of heptadecanoic acid and insulin, glucose, triglycerides and ferritin levels in sera for the MMP dolphins. To confirm this appreciation, the margaric acid levels of the sera in control population B (the Sarasota Bay dolphins) were checked.

Figure 5:
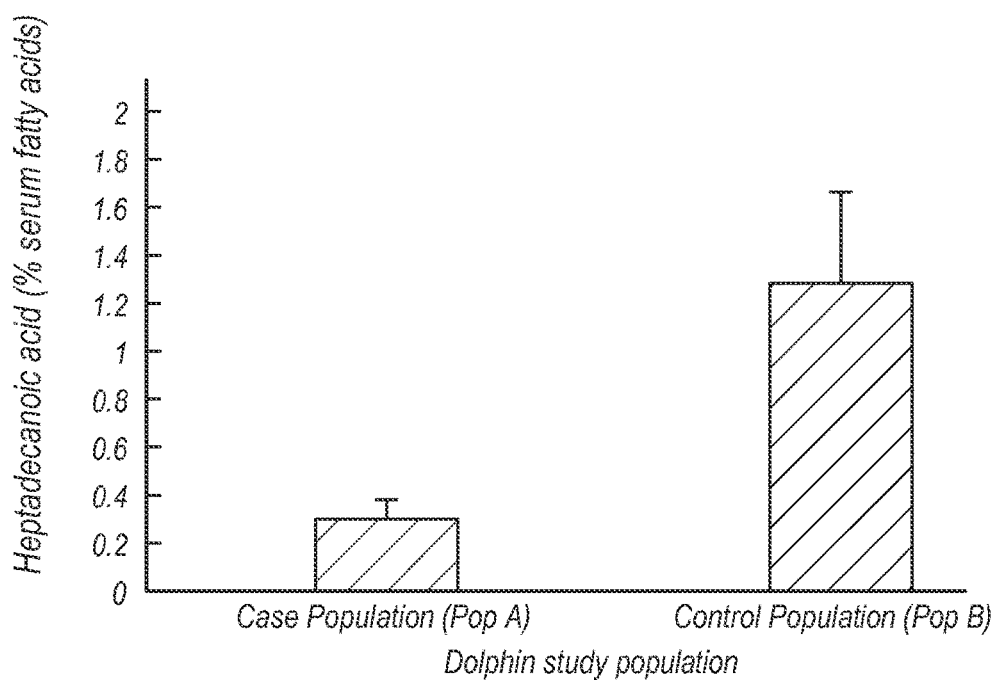
FIG. 5 is a comparison of sera heptadecanoic acid levels between a case study population of subjects that are highly susceptible to hyperferritinemia, iron overload, and metabolic syndrome (elevated insulin, glucose, and triglycerides) and a control study population with low susceptibility to hyperferritinemia and metabolic syndrome.

FIG. 5 illustrates the results of the above heptadecanoic acid check. From FIG. 5, it can be seen that the control population of Sarasota Bay dolphins had three times the level of heptadecanoic acid (measured as a percent serum fatty acid) than the case population A of MMP dolphins. Table 2 below illustrates a comparison of the blood samples of the above-cited 30 MMP dolphin versus the sera of 19 wild dolphins in their natural habitat (Sarasota Bay dolphins). MMP dolphins were older than Sarasota Bay dolphins (mean age±SD=25.6±12.2 and 12.7±9.0 years, respectively; P=0.002). As shown in Table 2, MMP dolphins had higher insulin, glucose, triglycerides, ferritin, iron, and transferrin saturation compared to Sarasota Bay dolphins. MMP dolphins had lower serum heptadecanoic acid when compared to Sarasota Bay dolphins. While red blood cell fatty acids were not collected on the initial group of 30 MMP dolphins, this measurement was included for Sarasota Bay dolphins to use as a reference during the subsequent feeding study with MMP dolphins, as described more fully below.

TABLE 2

| Blood-based variable | MMP (n = 30) | Sarasota Bay (n = 19) | P value |
| --- | --- | --- | --- |
| Metabolic variable | | | |
| Total insulin (µIU/ml) | 11 ± 12 | 2 ± 5 | <0.0001 |
| Glucose (mg/dl) | 117 ± 10 | 104 ± 15 | 0.005 |
| Triglycerides (mg/dl) | 148 ± 59 | 78 ± 26 | <0.0001 |
| Gamma-glutamyl transpeptidase (U/L) | 27 ± 11 | 20 ± 6 | 0.02 |
| Ferritin (ng/ml) | 3,878 ± 3,754 | 219 ± 184 | <0.0001 |
| Iron (µg/dl) | 177 ± 57 | 109 ± 48 | <0.0001 |
| Transferrin saturation (%) | 56 ± 20 | 33 ± 11 | <0.0001 |
| Targeted serum fatty acid (µg/ml) | | | |
| Heptadecanoic acid (C17:0) | 9 ± 2 | 25 ± 9 | <0.0001 |

From the above Table 2 data, it can be seen that among Sarasota Bay dolphins, serum heptadecanoic acid (µg/ml) was inversely associated with ferritin (R2=0.29 P=0.02). All Sarasota Bay dolphins with ferritin greater than 219 ng/ml (this population's 50th quartile) had serum heptadecanoic acid levels less than 25 µg/ml, suggesting that serum heptadecanoic acid lower than 25 µg/ml may result in an increased risk of hyperferritinemia.

Figure 6:
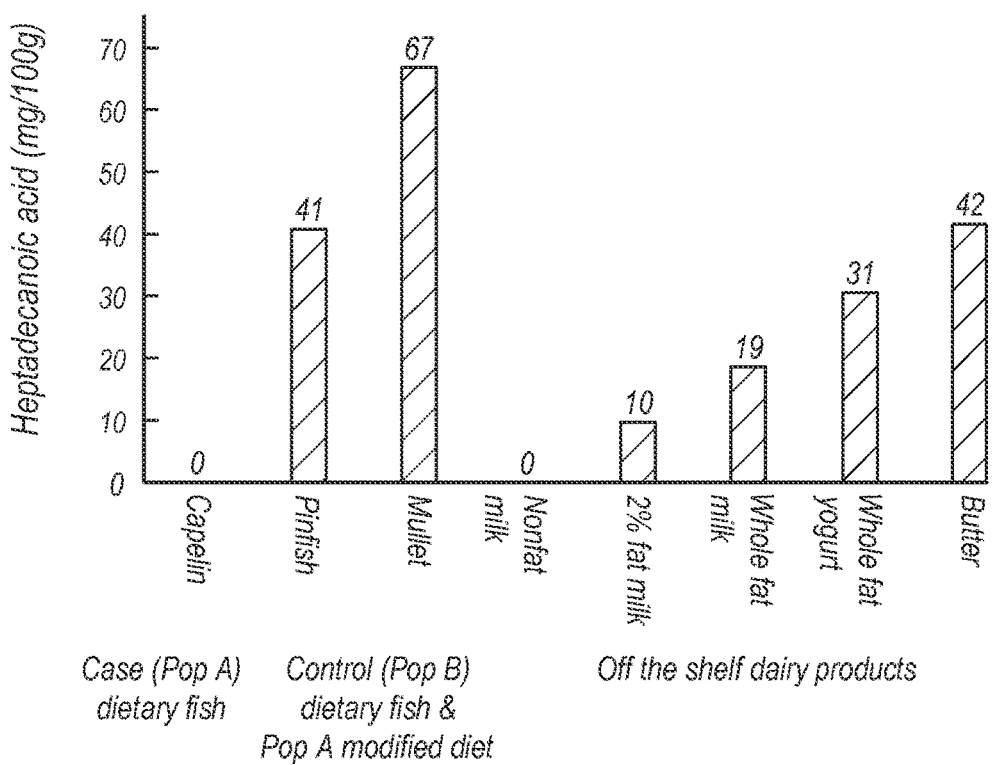
FIG. 6 is a bar graph that illustrates the amount (mg/100 g) of heptadecanoic acid in a variety of fish types and dairy products.

With a renewed focus on heptadecanoic acid, and referring now to FIG. 6, comparisons of diets of MMP dolphins (Case Population A) with diets of Sarasota Bay dolphins (Control Population B) were accomplished to determine the levels of heptadecanoic acid in the food being eaten by the two populations. As shown in FIG. 6, capelin, and the primary fish type fed to MMP dolphins, had no detectable heptadecanoic acid compared to other fish types. With the exception of squid (not shown in FIG. 6), capelin also had the lowest levels of iron compared to the other fish types. As shown in FIG. 6, mullet, and pinfish (which are representative of fish eaten by Sarasota Bay dolphins), had relatively high levels of heptadecanoic acid. Mullet and pinfish also had the highest iron levels among the fish tested. Due to the known presence of heptadecanoic acid in dairy products, heptadecanoic acid levels were measured in off-the-shelf dairy products. Dairy products consumed by human are also shown in FIG. 6, for comparison. The content of heptadecanoic acid (mg/100 g), from highest to lowest, was 42 (butter), 31 (whole fat yogurt), 19 (whole fat milk), and 10 (2% fat milk). Heptadecanoic acid was not detected in either nonfat milk <2 mg/100 g or nonfat yogurt <10 mg/100 g.

From the above data, it can be seen that there is a linear relationship between heptadecanoic acid and triglycerides, glucose, insulin and ferritin in sera, which has been confirmed with measurements of both heptadecanoic acid in dolphins for both a case population and a control population, as well as a measure of heptadecanoic acid in the diets eaten by the respective populations.

Figure 7:
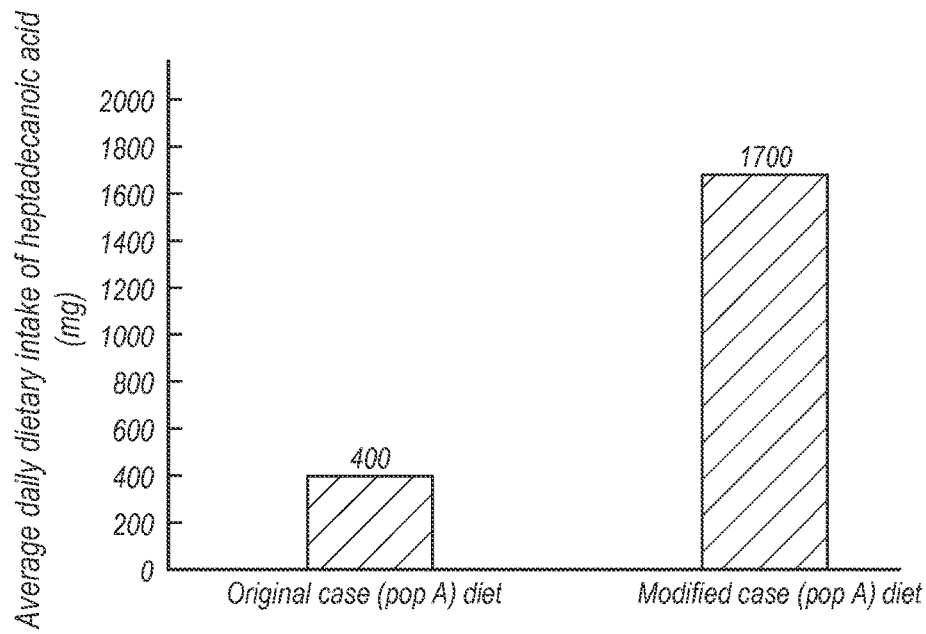
FIG. 7 is a bar graph that illustrates the comparison of total average daily dietary intake of heptadecanoic acid in the original versus modified diet for the feeding study supporting the claimed invention according to several embodiments.

Building on the above results, a 24-week feeding study was accomplished on the case population (MMP) dolphins, to determine if the above-referenced triglycerides, glucose, insulin, and ferritin sera levels could be manipulated by manipulating the C17:0 sera levels. To do this, the diets of the case population MMP dolphins were manipulated. More specifically, the diets of six MMP dolphins were modified to decrease capelin and introduce pinfish or mullet (fish with an increased amount of margaric acid) to their diet while maintaining the same diet caloric intake. Stated differently, and as shown in FIG. 7, the average daily intake of heptadecanoic acid was increased from approximately 400 mg to 1700 mg. The increase to 1700±500 mg daily heptadecanoic acid was equal to an approximate minimum daily heptadecanoic acid intake of 3 mg/lb body weight (6 mg/kg body weight). It should be appreciated however, that more research is needed to determine the exact minimum daily amount, and the minimum daily amount may go down or up according to future research. To evaluate potential confounding effects of the environment outside of the feeding study on the dolphins, eight MMP dolphins, which were housed in the same environment but not included in the feeding study, were monitored as references; these dolphins also had routine monthly blood samples collected during months 0, 1, 3, 4, and 6.

Figure 8:
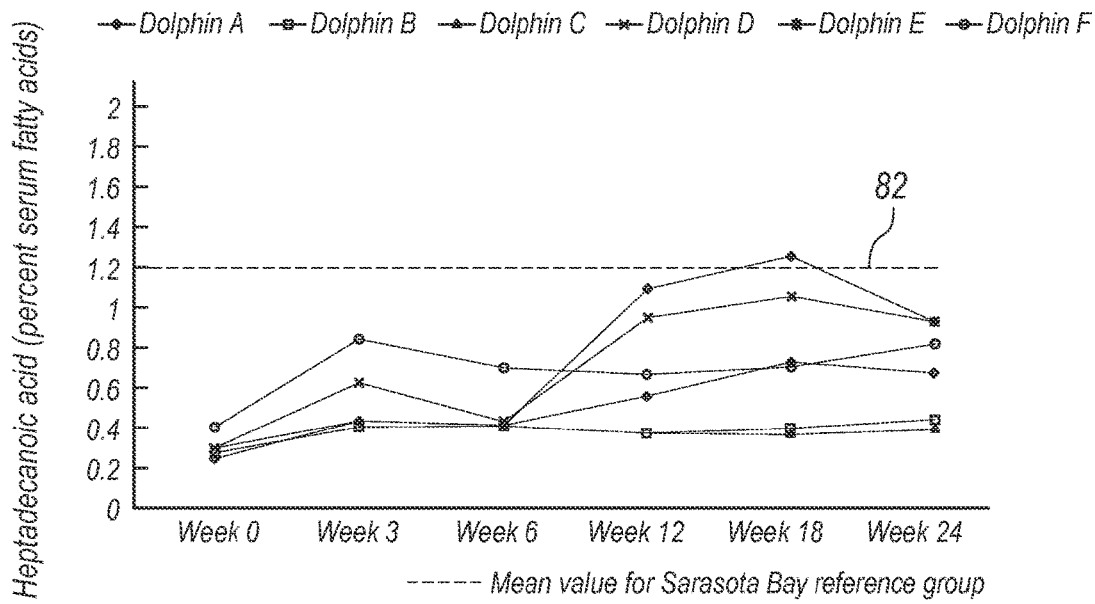
FIGS. 8-9 are graphs that illustrate the effects of the diet depicted in FIG. 7 on an increasing heptadecanoic acid in both subject sera (%) and subject red blood cell (RBC) membranes (µg/ml) during a 24-week feeding study.
Figure 9:
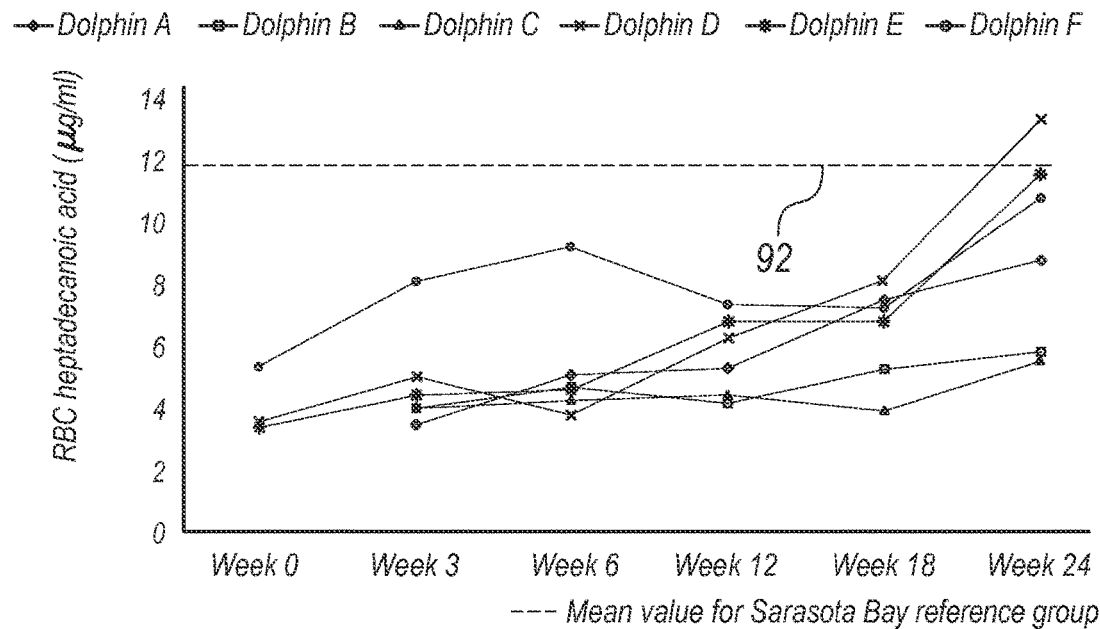

FIGS. 8 and 9 are graphs of sera heptadecanoic acid (as a percent serum fatty acid and RBC in µg/ml, respectively) for the MMP dolphins resulting from the above-described feeding study. Additionally, mean levels of margaric acid in Sarasota Bay dolphins (indicated by lines 82 and 92 in FIGS.

8-9) are included as a comparison. As can be seen in FIG. 8-9, as a result of the increase in heptadecanoic acid intake, serum levels of heptadecanoic acid were higher in feeding study dolphins during weeks 3, 6, 12, 18, and 24 when compared to week 0.

Figure 10:
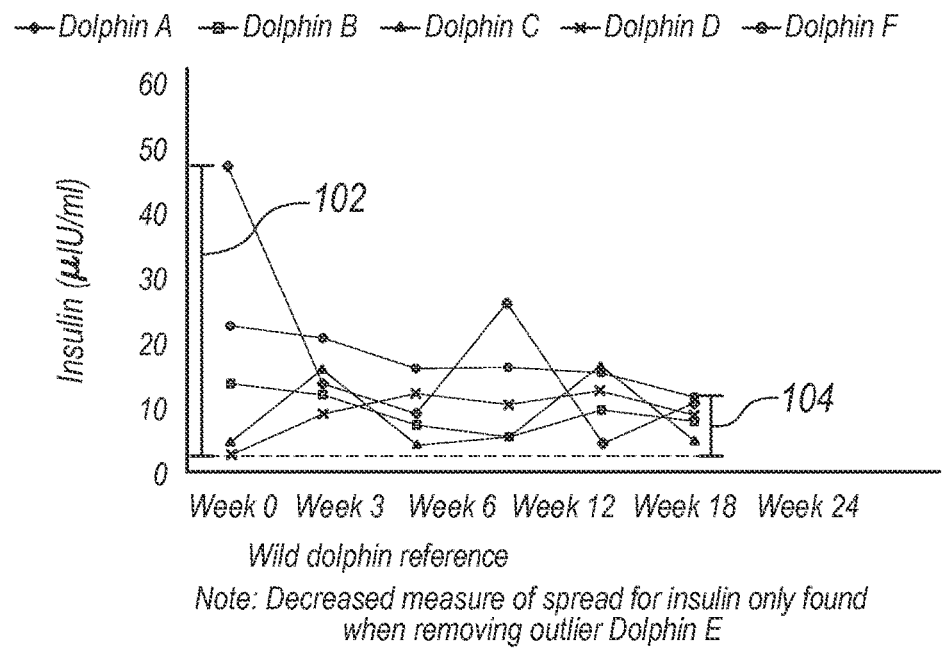
FIG. 10 is a graph that illustrates the effects of the diet on sera insulin levels for the subjects of the feeding study.

To determine the effects of increased sera heptadecanoic acid depicted in FIGS. 8-9, the insulin in the feeding study dolphins was measured. The measurement results are depicted in FIG. 10. As shown in FIG. 10, the insulin levels of the feeding study dolphins decreased during the period of the feeding study, which confirms the effects of the increased margaric acid in the subject sera. In addition, and perhaps just as importantly, a normalization of spread of insulin values for the subject sera was observed from an initial spread illustrated by line 102 at the start of the study (0 weeks) to a final spread 104 at 24 weeks.

Figure 11:
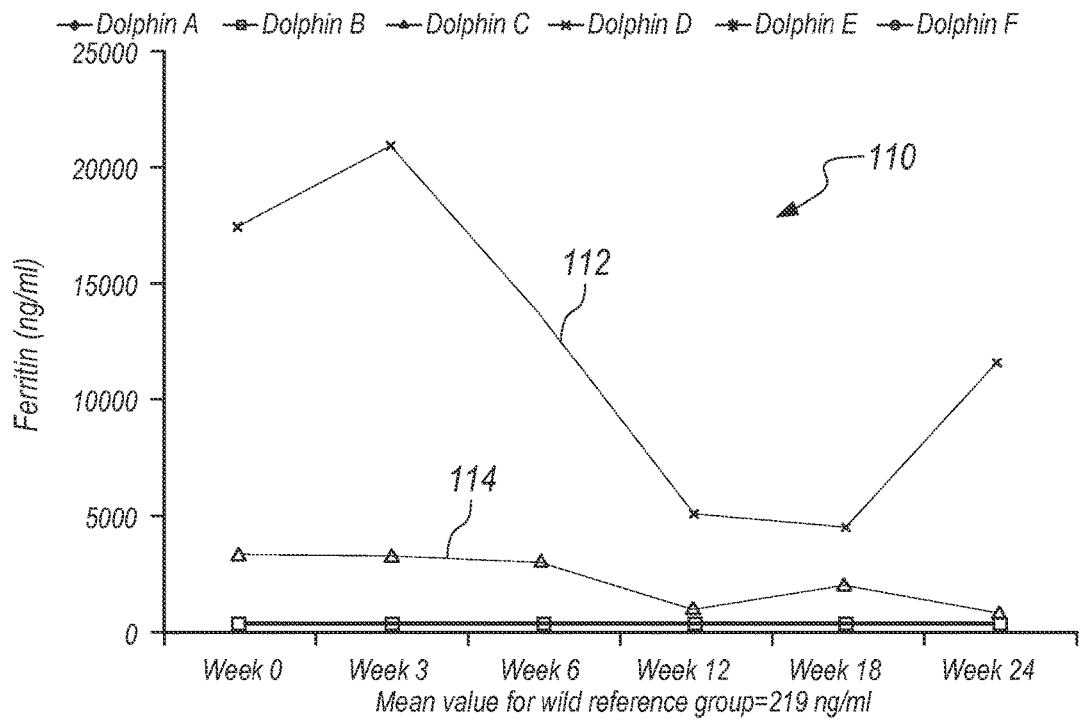
FIGS. 11-12 are graphs that illustrate the effects of the diet depicted in FIG. 7 on a decreasing sera ferritin levels during a 24-week feeding study.
Figure 12:
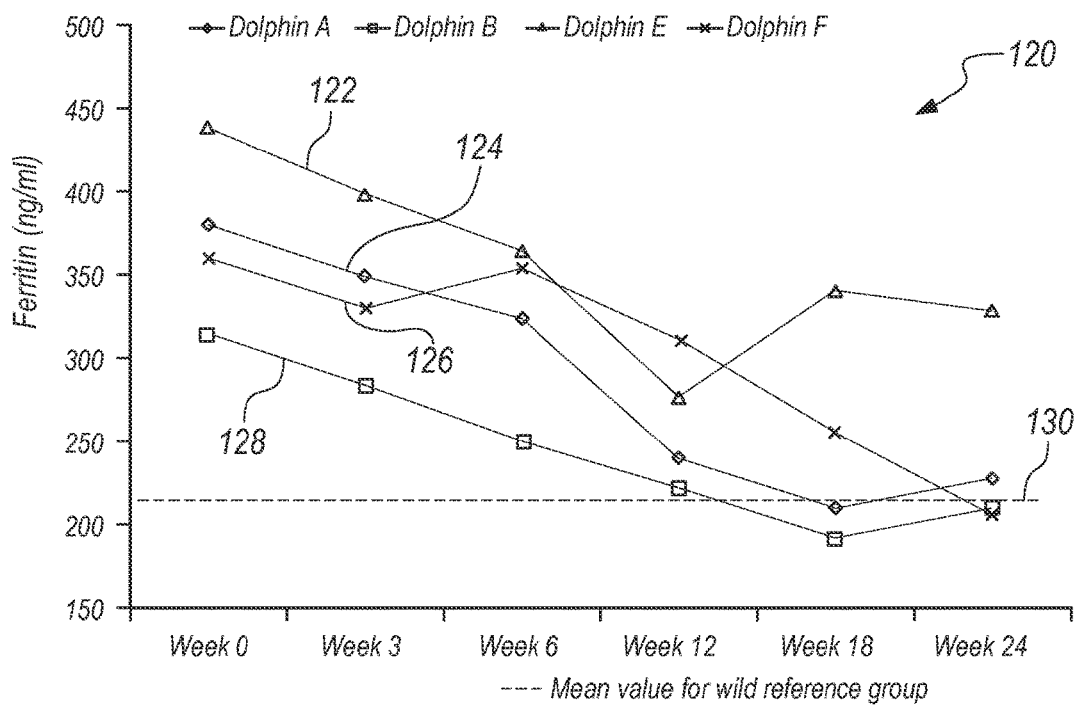

To determine the effects of increased sera margaric acid depicted in FIGS. 8-9 on ferritin levels, and referring now to graphs 110 and 120 in respective FIGS. 11 and 12, the ferritin in the feeding study dolphins was measured. As shown in FIGS. 11 and 12, serum ferritin levels continually decreased in all six dolphins throughout the feeding study, with weeks 3 through 24 having lower levels than week 0. Excluding the two extremely high ferritin outliers depicted by lines 112 and 114 in FIG. 10 (ferritin levels in the upper thousands to tens of thousands); the remaining dolphins (represented by lines 122, 124, 126 and 128 in FIG. 11) had the lowest mean serum ferritin (243±58 ng/ml) by week 24. Moreover, the mean ferritin levels for these dolphins approached the Sarasota Bay dolphins' mean value of 219±184 ng/ml, as depicted by line 130 in FIG. 11 (For purposes of the specification a therapeutic level can be defined as the mean level of Sarasota Bay dolphins). Due to the dramatic decrease in serum ferritin in all six feeding study dolphins, indices of acute inflammation (ceruloplamsin and haptoglobin) were assessed. Despite decreases in ferritin, there were no differences in these two proteins during any of the study weeks compared to week 0, supporting a conclusion that the decreased ferritin was not due to decreased acute inflammation.

Figure 13:
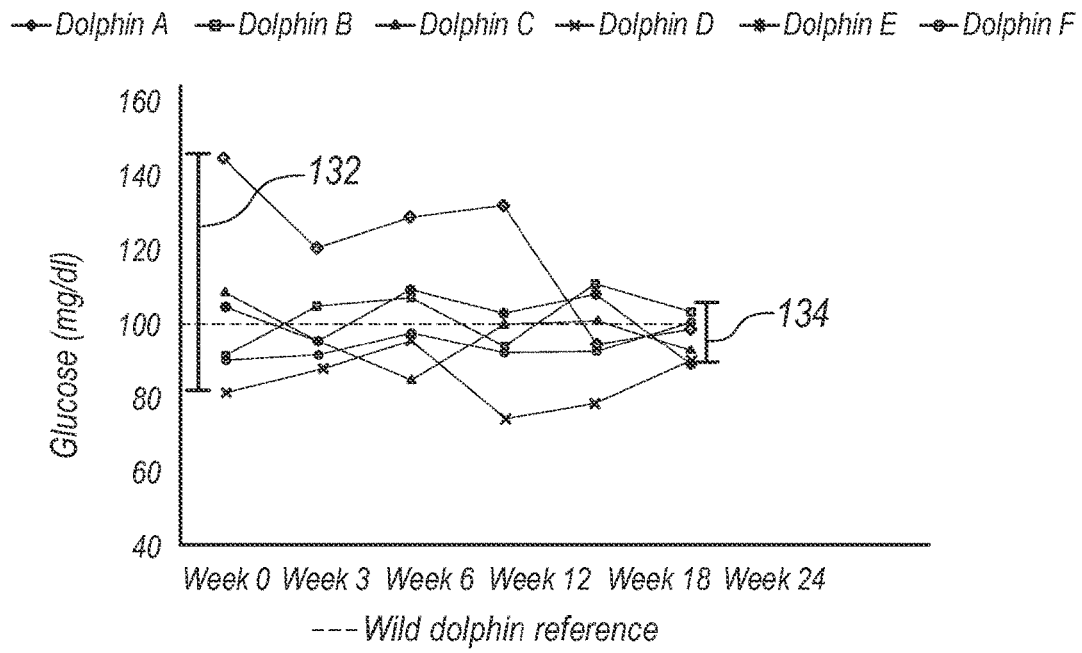
FIGS. 13-14 are graphs that illustrate the effects of the diet on sera glucose, and triglyceride levels for the subjects of the feeding study.
Figure 14:
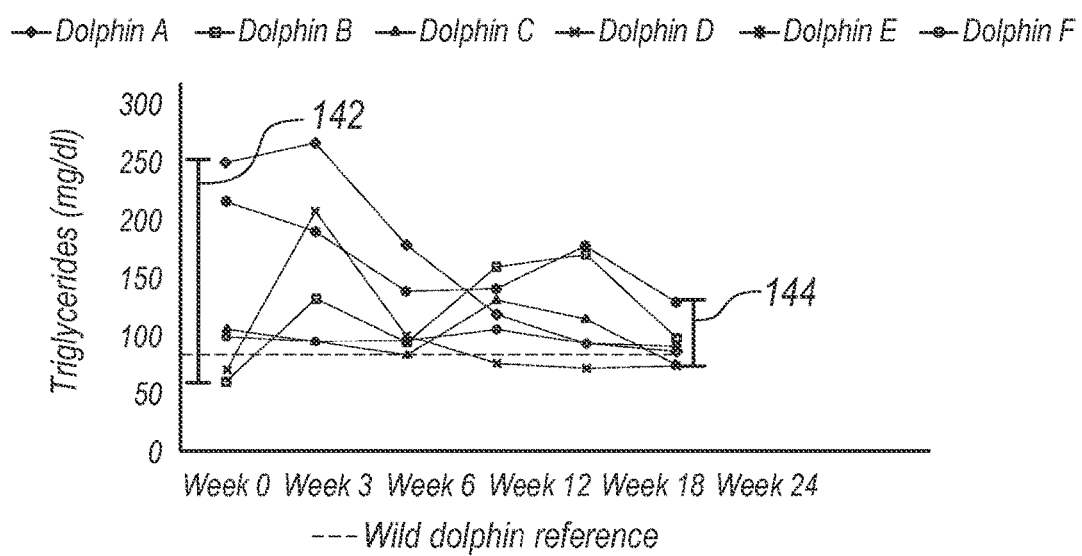

In addition to the decrease in ferritin, and referring now to FIGS. 10, 13 and 14, there was a distinct decrease in measures of spread for insulin, glucose, and triglycerides that trended from weeks 0 to 24, i.e., there was a normalization of insulin, glucose and triglycerides level in subject sera. Changes in serum insulin, glucose, triglycerides, and ferritin during week 0 were compared to weeks 3, 6, 12, 18 and 24 values were compared to week 0 using pairwise comparison t-tests (in the reference population, month 0 values were compared to months 1, 3, 4 and 6). Given the apparent tightening or normalization of glucose, triglycerides, and insulin (5 of 6 dolphins) values among feeding study dolphins by week 24, measures of spread (standard deviation, SD, and coefficient of variance, CV) were compared between weeks 0 and 24 for glucose, triglycerides, and insulin; outcomes were compared to the reference dolphin group. CV was calculated as follows: standard deviation÷mean).

With regard to decreasing measures of spread, the insulin standard deviation (FIG. 10) decreased from about 50 to about 12 µIU/ml, while the standard deviation for glucose (FIG. 13) decreased from approximately 70 to 20 mg/dl. The standard deviation for triglycerides (FIG. 14) decreased from about 200 to 90 mg/dl. The coefficient of variation (C.V.) from week 0 to week 24 decreased from 22% to 6% for glucose and 61% to 24% for triglycerides. When limiting to five study dolphins (excluding the outlier sixth dolphin), the insulin C.V. decreased from 100% to 38%. The decrease in measures of spread for these three key variables (normalization) is visually apparent from lines 102 and 104 in FIG. 10, initial spread 132 and final spread 134 in FIG. 13, and respective initial and final spreads 142 and 144 in FIG. 14.

Among the reference dolphin group for the feeding study (dolphins whose diet was not modified), there was not a difference in serum ferritin (week 0=4,116±2,822 ng/ml) compared to weeks 3, 12, and 18 (4,433±3,000, 4,055±2,534, and 3,418±2,059 ng/ml respectively; P=0.43, 0.92, and 0.37). There were also no differences in glucose and triglycerides when comparing week 0 with weeks 3, 12, and 18 (not shown); and the measures of spread for glucose and triglycerides did not decrease from week 0 to week 18 (standard deviation=16 and 15 mg/dl, C.V.=16% and 15% for glucose; and 58 and 48 mg/dl, C.V.=74% and 66% for triglycerides, respectively). Similarly, serum heptadecanoic acid (9.3±4 versus 9.3±4 ng/dl; P=0.98) glucose, and triglycerides did not differ in mean or measures of spread for the reference population when comparing month 0 with month 4.

While not statistically significantly different using the applied methods based upon the mean, mean levels of all three indicators of metabolic syndrome did trend down; for week 0 versus week 24, mean insulin decreased from 24 to 16 µIU/ml, glucose from 105 to 95 mg/dl, and triglycerides from 132 to 87 mg/dl. In sum, FIGS. 10-14 can be taken to mean that increased levels of heptadecanoic acid can result in a decrease of ferritin levels and a normalization of metabolic syndrome biomarkers in subject sera.

This is the first report of heptadecanoic acid as an independent predictor among a full suite of metabolic syndrome indices, including glucose, insulin, triglycerides, and associated ferritin. Importantly, when dolphins with hyperferritinemia increased their dietary intake of heptadecanoic acid by changing fish types fed, ferritin, glucose, triglycerides, and insulin normalized by week 24. Because hyperferritinemia in humans is associated with metabolic syndrome, and resolution of iron overload with phlebotomy improves insulin resistance, this study may provide important insight into how heptadecanoic acid deficiencies may be an underlying and treatable cause of hyperferritinemia and subsequent metabolic syndrome in humans.

Heptadecanoic acid (C17:0), also called margaric acid, is a saturated fatty acid present in bovine milk fat and was the original component of margarine (hence, margarine's name) in the late 1800s. Heptadecanoic acid in margarine, however, was replaced with less costly and more readily available plant-based and trans-fatty acids. When off the shelf dairy products were tested in the current study, heptadecanoic acid was highest in butter and whole fat yogurt and absent in nonfat dairy products. Interestingly, despite consumer's movement away from high fat foods, dairy consumption in humans has been associated with multiple health benefits, including lower risks of insulin resistance syndrome, metabolic syndrome, and type 2 diabetes. To date, the mechanism of the benefits of dairy products on human metabolism has not been determined. Based upon the results using the methods of the present invention, it can be proposed that heptadecanoic acid may be a key player in the metabolic benefits of dairy products in humans. To take advantage of these benefits, heptadecanoic acid can be used in aid in a supplement, food additive, food fortifier, beverage additive, beverage fortifier, or pharmaceutical in any form, including as a tablet, encapsulated pill, gelcap pill, liquid suspension, spray, and powder. Additionally, diagnostic tests and assays for heptadecanoic acid in human and animal samples (including blood (serum, plasma, and erythrocyte membranes), urine, and feces) can be used to detect low heptadecanoic acid levels and to continually monitor heptadecanoic acid levels in patients. The use of heptadecanoic acid can prevent, stem, and treat: 1) Elevated ferritin and associated complications, including iron overload, metabolic syndrome, type 2 diabetes, autoimmune diseases, and neurodegenerative diseases (including but not limited to Alzheimer's disease, Parkinson's disease, and restless leg syndrome); and, 2) Metabolic syndrome components and associated complications, including dyslipidemia, hypertriglyceridemia, elevated glucose, elevated insulin, type 2 diabetes, heart disease, and stroke. These egregious health effects can be prevented not only in dolphins, but because of the similarities in blood panels, they can be prevented in human mammals as well.

Figure 15:
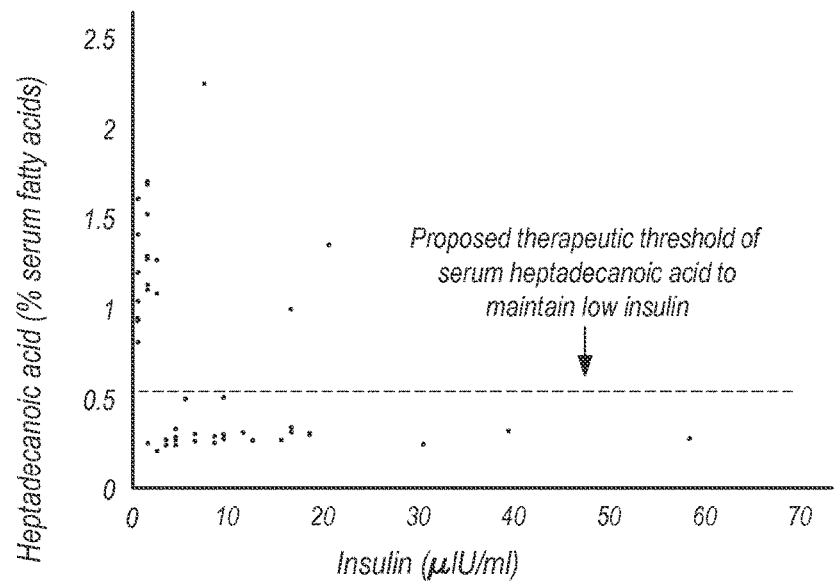
FIG. 15 is a scatter plot of heptadecanoic acid (% serum fatty acids) versus insulin in both case and control populations, which indicates therapeutic thresholds of heptadecanoic acid for the present invention according to several embodiments; and, FIG. 16 is a scatter plot of heptadecanoic acid (% serum fatty acids) versus ferritin, which indicates therapeutic thresholds of heptadecanoic acid for the present invention according to several embodiments.

Referring now to FIG. 15, scatter plots of heptadecanoic acid versus insulin for both the control populations and the study populations is shown. As shown in FIG. 15, using a proposed therapeutic threshold of serum heptadecanoic of 0.4 percent as percent of the total fatty acid in serums, can maintain a low insulin (as defined above) level.

It is unknown precisely how high ferritin increases the risk of diabetes, but proposed mechanisms include direct injury to the liver and pancreas from excessive deposition or indirect injury from increased oxidative radicals. Currently, the most accepted means of treating hyperferritinemia and associated iron overload in humans is phlebotomy (removal of iron in the blood). The methods according to several embodiments describe methods wherein hyperferritinemia that is associated with prediabetes can be reversible using a modified diet most likely involving increased dietary intake of heptadecanoic acid. Reversal of hyperferritinemia by week 3 using the modified diet was followed by normalization of prediabetes/metabolic syndrome (normalized glucose, insulin, and triglycerides) at week 24, as described above. In fact, the methods of the present invention can be used to treat hyperferritinemia with requiring phlebotomy.

Figure 16:
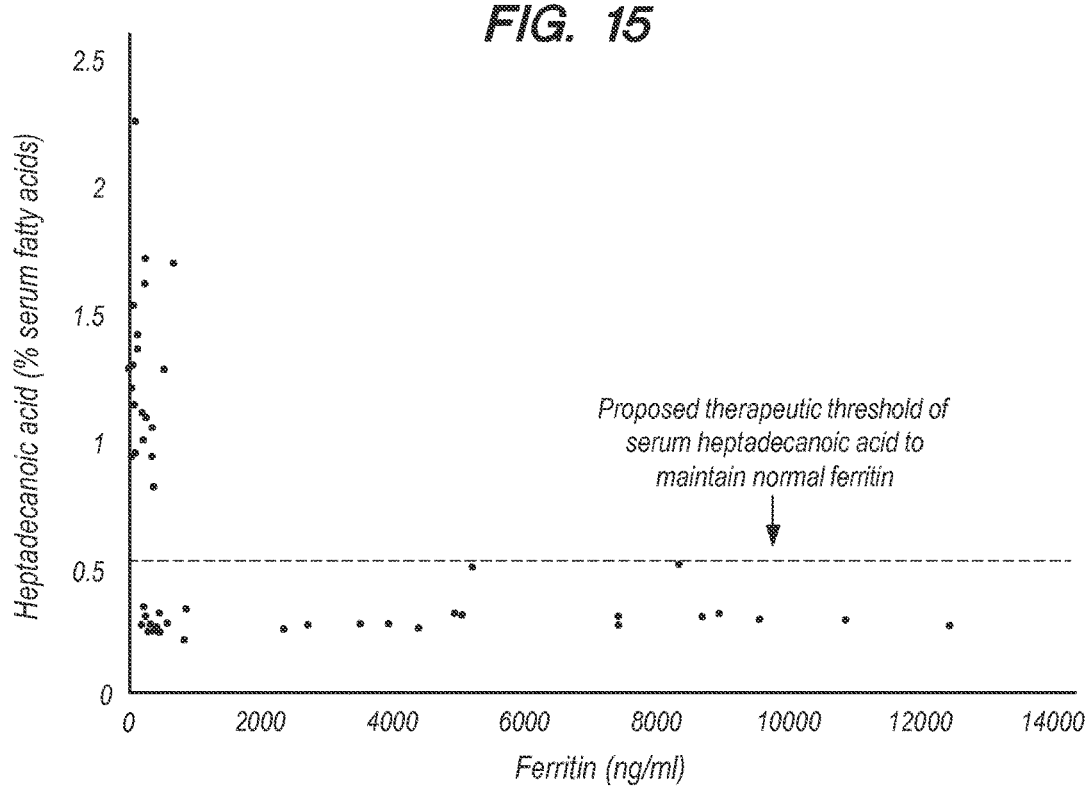

Referring now to FIG. 16, scatter plots of heptadecanoic acid versus ferritin levels for both the control populations and the study populations is shown. As shown in FIG. 16, using a proposed therapeutic threshold of serum heptadecanoic of 0.4 percent as percent of the total fatty acid in serums, can also maintain a therapeutic ferritin (as defined above) level.

There are several limitations to the current study. First, study dolphins from MMP and Sarasota Bay live in the open ocean, and known dietary intake was limited to fish fed to MMP dolphins. MMP dolphins live in netted enclosures in San Diego Bay, and changing populations of local fish are readily available to eat. While MMP dolphins can eat local fish, however, observation of feeding behaviors by MMP's animal care staff and maintained dolphin appetites for fed fish support that the majority of dietary fish are those that are fed by the MMP. Reference dolphins in the same population and environment, however, did not have the same decreases in serum ferritin and normalization of glucose and triglycerides. Second, the proposed direct effect of heptadecanoic acid on lowering high serum ferritin has to be interpreted with caution because the feeding study involved fish with higher heptadecanoic acid. The potential impact (or cumulative impacts) of other nutrients in the modified diet on serum ferritin cannot be ruled out until feeding studies are limited to a heptadecanoic acid supplement. Identification of 1) higher serum percent heptadecanoic acid as an independent predictor of lower serum ferritin, 2) demonstrated increased dietary intake and percent serum heptadecanoic acid during the feeding study, and 3) coincident decreases in serum ferritin and increases in percent serum heptadecanoic acid by week 3, however, provide evidence that increasing dietary heptadecanoic acid contributed to decreased serum ferritin.

In conclusion, this study with dolphins is the first to propose heptadecanoic acid deficiencies as a means to detect a risk of or cause for metabolic syndrome and associated hyperferritinemia. Further, dietary supplementation with heptadecanoic acid may help resolve both conditions. Future research with human populations is needed to assess similar relationships between heptadecanoic acid, serum ferritin, metabolic syndrome, and type 2 diabetes. Further, given hyperferritinemia's association with autoimmunity in humans, this invention (use of heptadecanoic acid deficiency detection and resolution as a means to prevent or manage disease) could also apply to type 1 diabetes, an autoimmune disease. Successful demonstration of these links in humans would support our hypothesis that widespread movement away from high fat dairy products in some countries and decreasing frequencies of fish meals in other countries have led to heptadecanoic acid deficiencies globally, which may be contributing to an increasing prevalence of hyperferritinemia, metabolic syndrome, and the diabetes pandemic.

The use of the terms "a" and "an" and "the" and similar references in the context of describing the invention (especially in the context of the following claims) is to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating hyperferritinemia comprising the step of administering a daily dose of heptadecanoic acid to a subject suffering from hyperferritinemia for a period of time from three weeks to twenty-four weeks, wherein said minimum daily dose comprises about 3 mg per lb (or 6 mg per kg) of body weight.

2. The method of claim 1, wherein said method is accomplished without phlebotomy.

* * * * *